United States Patent [19]

Kozikowski

[11] Patent Number: 4,988,682

[45] Date of Patent: Jan. 29, 1991

[54] MYO-INOSITOL ANALOGS AND METHOD FOR THEIR USE

[75] Inventor: Alan P. Kozikowski, Ponte Verda Beach, Fla.

[73] Assignee: University of Pittsburgh, Pittsburgh, Pa.

[21] Appl. No.: 306,728

[22] Filed: Feb. 3, 1989

[51] Int. Cl.$^5$ .............................................. A61K 31/655
[52] U.S. Cl. .................... 514/150; 514/579; 514/706; 514/715; 514/729; 558/431; 564/462; 568/62; 568/833; 552/1; 562/899
[58] Field of Search .................. 568/833, 62; 514/715, 514/150, 579, 706, 729; 260/349, 550; 558/431; 564/462

[56] References Cited

U.S. PATENT DOCUMENTS

| | | | |
|---|---|---|---|
| 3,887,590 | 6/1975 | Cier et al. | 260/349 |
| 4,474,806 | 10/1984 | Beattie et al. | 424/300 |
| 4,515,722 | 5/1985 | Yang et al. | 260/403 |

OTHER PUBLICATIONS

McCasland et al., J. Org. Chem. 28(8), pp. 2096–2101 (1963).
J. Gigg et al, *The Allyl Group for Protection and Carbohydrate Chemistry, Part 18, Allyl and Benzyl Ethers of Myo-Inositol, Intermediates for the Synthesis of Myo-Inositol Trisphosphates,* Journal Chemical Society Perkin Trans., 423–429 (1987).
S. S. Yang et al., *DAST–Induced Epimerization of a 2-(acetoxymethyl),* Journal Organic Chemistry, 46, 1718–1720 (1981).
W. J. Middleton, *New Flurinating Reagents, Dialkylaminosulphur Fluorides,* Journal Organic Chemistry, 40, 574–578 (1975).
S. S. Yang et al., *Synthesis of 2-ax-Fluror-2-eq-Hydroxymethyl-2-deoxymyoinositol,* Synthetic Communications 16, 131–138 (1986).
C. Jiang et al., *Synthesis of Deoxy and Deoxy-Halogeno Analogues of MyoInositol,* Journal Carbohydrate Chemistry, 6, 319–355 (1987).
S. Ozaki, *Synthesis of D-Myo-Inositol 1,3,4,5-Tetrakisphosphate,* Tetrahedron Letters, 28, 4691–4694 (1987).
S. S. Yang et al., *Synthesis of Fluorodeoxy-Scylloinositol and Phosphatidylfluorodeoxyscylloinositol,* Tetrahedron Letters, 23, 5517–5520 (1982).
M. Hamblin et al., *Biophosphorylation of a Vic-Diol Using a Phosphite Approach: Synthesis of Myo-Inositol 4,5-Bisphosphate,* Journal Chem. Society, Chem. Communications, 626–627 (1987).
J. P. Vacca et al., *Total Synthesis of D-and L-Myo-Inositol 1,4,5-Trisphosphate, Journal American Chemical Society,* 109, 3478–3479 (1987).
S. P. Ozaki et al., *Total Synthesis of Optically Active Myo-Inositol 1,4,5-Tris(Phosphate),* Tetrahedron Letters, 27, 3157–3160 (1986).
D. Billington et al., *Synthesis of Myo-Inositol 1,3,4,5-Tetraphosphate and Myo-Inositol 1,3-Bisphosphate,* Journal Chemical Society, Chem Communications, 1011–1013 (1987).
Y. Watanabe et al., *Stepwise Phosphorylation of Vicinal Diol and Sterically Hindered Alcohol directed Toward D Myo Inositol 2,4,5-Trisphosphate,* Tetrahedron Letters, 28, 2607–2610 (1987).
C. B. Reese et al., *Synthesis of D-Myo-Inositol 1,4,5--Trisphosphate,* Tetrahedron Letters, 28, 2309–2312 (1987).
J. D. Moyer et al., *Substrate Properties of Analogs of Myo-Inositol,* Molecular Pharmacology, 33, 683–689 (1988).
M. A. Polokoff et al., *Metabolism of Synthetic Inositol Triphosphate Analogs,* The Journal of Biological Chemistry, 263, 11922–11927 (1988).
T. A. Suami et al., *Inositol Derivatives, 7, Azidolysis of Disulfonate of Myo-Inositol and 1,2-O-Cyclohexylidine Derivative,* Bulletin of the Chemical Society of Japan, 47, 1731–1736 (1974).
N. Kurihara et al., *Chemistry of Benzene Glycols, Part XVII, A New Synthesis of Streptamine,* Agra. Biol. Chem., 31, 1166–1170 (1967).
S. J. deSolms, *The Total Synthesis of (±)-Myo-Inositol-1,3,4-Trisphosphate, (±)-Myo-Inositol 1,3,4,5-Tetrikisphosphate,* Tetrahedron Letters, 28, 4503–4506 (1987).
A. P. Kozikowski et al., *A Synthesis of (−)-1L-1-Deoxy-1-Fluoro-Myo-Inositol; a Compound of Potential Use in sorting Out the Phosphatidylinositol Response,* J. Chem. Soc., Chem., Commun., 1301–1303 (1988).
M. F. Boehm et al., *Fluorinated Analogs and Tritiated Enantiomers of Inositol (1,3,4)-Trisphosphate,* Tetrahedron Letters, vol. 29, 41 5217–5220 (1988).
M. J. Berridge et al., *Inositol Trisphosphate, A Novel Second Messenger in Cellular Signal Transduction, Nature,* vol. 312, 315–321 (1984).
M. Whitman et al., *Type I Phosphatidylinositol Kinase Makes a Novel Inositol Phospholipid, Phosphatidylinositol-3-Phosphate, Nature,* vol. 312, 644–647 (1988).

*Primary Examiner*—Bruce Gray
*Attorney, Agent, or Firm*—Pennie & Edmonds

[57] ABSTRACT

The present invention relates to a method for inhibiting the phosphatidylinositol cycle in a cell by contacting the cell with certain myo-inositol analogs. Such myo-inositol analogs can also be utilized to treat phosphatidylinositol cycle-dependent conditions. The present invention also provides novel myo-inositol analogs.

16 Claims, No Drawings

4,988,682

MYO-INOSITOL ANALOGS AND METHOD FOR THEIR USE

TABLE OF CONTENTS

1. Technical Field
2. Background of the Invention
3. Summary of the Invention
4. Detailed Description of the Invention
4.1 The Method of the Invention
   4.1.1 In-Vitro Method
   4.1.2 In-Vivo method
4.2 Compounds of the Present Invention
4.3 Mode of Administration and Pharmaceutical Compositions
5. Examples
5.1 Synthesis of Compounds of Formula I
5.2 Biological Data

1. TECHNICAL FIELD

The present invention relates to a method for inhibiting the phosphatidylinositol cycle in a cell by contacting the cell with certain myo-inositol analogs. Such myo-inositol analogs can also be utilized to treat phosphatidylinositol cycle-dependent conditions. The present invention also provides novel myo-inositol analogs.

2. BACKGROUND OF THE INVENTION

For a cell to survive, it must be able to respond rapidly to changes in its environment. Furthermore, for cells to reproduce and carry out other co-operative functions, they must be able to communicate efficiently with each other. Cells most frequently adapt to their environment and communicate with one another by means of chemical signals. An important feature of these signaling mechanisms is that in almost all cases a cell is able to detect a chemical signal without it being necessary for the chemical messenger itself to enter the cell. This permits the cell to maintain tight control of its internal milieu, thereby permitting the cell to respond to its environment without being destroyed by it.

These sensing functions are carried out by a variety of receptors, which are dispersed on the outer surface of the cell and function as molecular antennae. These receptors detect an incoming messenger and activate a signal pathway that ultimately regulates a cellular process such as secretion, contraction, metabolism or growth. The major barrier to the flow of information is the cell's cellular plasma membrane, where transduction mechanisms translate external signals into internal signals, which are then carried throughout the interior of the cell by "second messengers."

In molecular terms, the process depends on a series of proteins within the cellular plasma membrane, each of which transmits information by inducing a conformational change—an alteration in shape and therefore in function—in the protein next in line. At some point the information is assigned to small molecules or even to ions within the cell's cytoplasm, which serve as the above-mentioned second messengers, whose diffusion enables a signal to propagate rapidly throughout the cell.

The number of second messengers appears at present to be surprisingly small. To put it another way, the internal signal pathways in cells are remarkably universal, and have been phylogenetically preserved over millions of years of evolution. Yet the known messengers are capable of regulating a vast variety of physiological and biochemical processes. The discovery of the identity of particular second-messenger substances is proving, therefore, to be of fundamental importance for understanding how cellular growth and function are regulated.

Several major signal pathways are now known, but two seem to be of primary importance. One employs cyclic nucleotides as second-messengers. These cyclic nucleotides activate a number of proteins inside the cell, which then cause a specific cellular response. The other major pathway employs a combination of second messengers that includes calcium ions as well as two substances whose origin is remarkable: inositol 1, 4, 5 triphosphate ($IP_3$) and diacylglycerol (DG). These compounds are cannibalized from the plasma membrane itself, by enzymes which are activated by specific cellular membrane receptors. However, it should be noted that inositol in its non-phosphorylated form first enters an organism through the organism's diet, but can then be recycled as described hereinbelow.

$IP_3$ is formed by the following scheme. A receptor molecule on the surface of the cellular plasma membrane transmits information through the cellular plasma membrane and into the cell by means of a family of G proteins, which are cellular plasma membrane proteins that cannot be active unless they bind to guanosine triphosphate (GTP). The G proteins activate the so-called "amplifier" enzyme phospholipase C, which is on the inner surface of the cellular plasma membrane. Phospholipase C cleaves the cellular plasma membrane lipid phosphatidylinositol 4, 5-bisphosphate ($PIP_2$) into DG and $IP_3$. $IP_3$ is a water-soluble molecule, and therefore, upon being released from the inner surface of the cellular plasma membrane, it rapidly diffuses into cytoplasm. $IP_3$ then releases calcium from internal compartments, which store high concentrations of calcium. The calcium released by $IP_3$ in turn activates a large number of intracellular enzymes that orchestrate a complex set of responses that allow the cell to adapt to the original signal triggering the receptor that caused the release of $IP_3$.

Quite fascinatingly, DG and $IP_3$ are recycled. DG is recycled by a series of chemical reactions which constitute one component of the lipid cycle. $IP_3$ is recycled by a series of reactions known as the phosphatidylinositol cycle. The two cycles converge at the point when inositol is chemically linked to DG. The DG-bound inositol is phosphorylated in a series of steps which ultimately results in the reformation of phosphatidylinositol diphosphate.

In the first portion of the lipid cycle, DG is converted to phosphatidic acid, which in turn is converted to cytidine diphosphate deglyceride (CDP—DG), while in the first portion of the phosphatidylinositol cycle, $IP_3$ is dephosphorylated to ultimately form myo-inositol. [Note: "myo" refers to the stereochemistry of the inositol molecules. Since all known inositol second messengers use the myo-configuration of inositol, the term "inositol" will herein be understood to refer to myo-inositol.] It is believed that such dephosphorylation occurs stepwise; $IP_3$ is converted to an inositol bearing only two phosphate groups ($IP_2$), followed by the loss of an additional phosphate, resulting in $IP_1$, which is then dephosphorylated to myo-inositol. Also, it has been shown that $IP_3$ can also undergo an additional phosphorylation, thereby being converted to inositol 1, 3, 4, 5 tetra-phosphate ($IP_4$). This molecule is subsequently metabolized by successive removal of phosphate groups, as described above. It is believed that a phosphatase enzyme catalyses each step of this process.

The lipid cycle and phosphatidylinositol cycle merge by the myo-inositol reacting with the CDP—DG to form phosphatidylinositol (PI). PI is phosphorylated to ultimately form $PIP_2$. It is believed that such phosphorylation occurs stepwise; PI is converted to phosphatidyl myo-inositol 4-phosphate (PIP), which is converted to $PIP_2$, the final step of both cycles. It is believed that a kinase enzyme catalyses each step of this process.

For an excellent review of $IP_3$, its role as a second messenger and the phosphatidylinositol cycle see Berridge, M., et al. *Inositol Triphosphate, a Novel Second Messenger in Cellular Signal Transduction*, Nature, 312, 315-321 (1984) and Berridge, M., *The Molecular Basis of Communication Within the Cell*, Scientific American, 142-152 (October 1985), and James W. Putney, Jr. (Ed.), *Phosphoinositides and Receptor Mechanisms*, Alan R. Liss, Inc., New York, N.Y. 1986.

3. SUMMARY OF THE INVENTION

The present invention relates to a method for inhibiting the phosphatidylinositol cycle in a cell which comprises contacting said cell with a compound represented by the formula I:

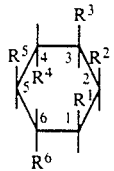

wherein:

$R^1$, $R^2$, $R^3$, $R^4$, $R^5$ and $R^6$ is each independently selected from the group consisting of OH, F, $N_3$, $NH_2$, SH, SeH, Cl, Br, I and CN; with the proviso:
 (i) four or five of said $R^1$, $R^2$, $R^3$, $R^4$, $R^5$ and $R^6$ are OH; and
 (ii) if said $R^4$, $R^5$ or $R^6$ is F, Cl, Br or I then four of said $R^1$, $R^2$, $R^3$, $R^4$, $R^5$ and $R^6$ are OH.

The present invention also provides a method for treating phosphatidylinositol cycle-dependent conditions.

The present invention also provides compounds represented by the formula II:

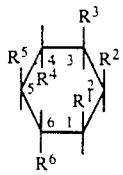

wherein:
$R^1$, $R^2$, $R^3$, $R^4$, $R^5$ and $R^6$ is each independently selected from the group consisting OH, F, $N_3$, $NH_2$, SH, SeH, Cl, Br, I and CN; with the proviso:
 (i) four or five of said $R^1$, $R^2$, $R^3$, $R^4$, $R^5$ and $R^6$ are OH;
 (ii) if one of said $R^1$, $R^2$, $R^3$, $R^4$, $R^5$ and $R^6$ is $N_3$, then one of said $R^1$, $R^2$, $R^3$, $R^4$, $R^5$ and $R^6$ is selected from the group consisting of F, $NH_2$, SH, SeH, Cl, Br, I and CN;
 (iii) if one of said $R^1$, $R^2$, $R^3$, $R^4$, $R^5$ and $R^6$ is $NH_2$, then one of said $R^1$, $R^2$, $R^3$, $R^4$, $R^5$ and $R^6$ is selected from the group consisting of F, $N_3$, SH, SeH, Cl, Br, I and CN; and
 (iv) if said $R^4$, $R^5$ or $R^6$ is F, Cl, Br or I then four of said $R^1$, $R^2$, $R^3$, $R^4$, $R^5$ and $R^6$ are OH.

4. DETAILED DESCRIPTION OF THE INVENTION

4.1 The Method of the Invention

The present invention relates to a method for inhibiting the phosphatidylinositol cycle in a cell which comprises contacting said cell with a compound represented by formula I:

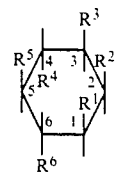

wherein:
$R^1$, $R^2$, $R^3$, $R^4$, $R^5$ and $R^6$ is each independently selected from the group consisting OH, F, $N_3$, $NH_2$, SH, SeH, Cl, Br, I and CN; with the proviso:
 (i) four or five of said $R^1$, $R^2$, $R^3$, $R^4$, $R^5$ and $R^6$ are OH; and
 (ii) if said $R^4$, $R^5$ or $R^6$ is F, Cl, Br or I then four of said $R^1$, $R^2$, $R^3$, $R^4$, $R^5$ and $R^6$ are OH.

It is believed that the compounds of formula I, which are analogs of myo-inositol, are effective for inhibiting the phosphatidylinositol cycle. Without being bound by theory, it is believed that the compounds of formula I inhibit the phosphatidylinositol cycle by two mechanisms. Firstly, the compounds of formula I compete with myo-inositol for being transported into the cell and, therefore, less myo-inositol is available in the cell to be utilized in the phosphatidylinositol cycle. Secondly, the phosphatase enzymes and kinase enzymes of the phosphatidylinositol cycle cannot dephosphorylate and phosphorylate, respectively, the positions of the compounds of formula I that are substituted with F, $N_3$, $NH_2$, SH, SeH, Cl, Br, I or CN, thereby inhibiting such enzymes from being utilized efficiently in the phosphatidylinositol cycle, thus inhibiting such cycle.

4.1.1 In-Vitro Method

This method can be carried out either in-vitro or in-vivo. In-vitro, the compounds of formula I can be utilized as pharmacological tools for studying cellular response to, for example, hormones, neuropeptides, neurotransmitters or synthetic drugs. Such compounds can also be utilized to study the involvement of the phosphatidylinositol cycle in cellular growth or cellular differentiation.

The compounds of formula I can also be radiolabeled, e.g., tritiated, which renders it easier to detect the presence of such compounds in cells. Also, radiolabeling can be utilized to study what proportion of the compounds of formula I enters the cells.

4.1.2. In-Vivo Method

The method can also be utilized in-vivo which comprises a method for inhibiting the phosphatidylinositol cycle in a mammal, including humans, which comprises administering to said mammal an phosphatidylinositol cycle inhibiting amount of a compound of formula I.

The present invention also covers the use of the compounds of formula I to treat phosphatidylinositol cycle-dependent conditions in mammals, including humans. This aspect of the present invention comprises a method for treating phosphatidylinositol cycle-dependent conditions in a mammal which comprises administering to said mammal an phosphatidylinositol cycle inhibiting amount of a compound of formula I.

Inositol phosphate cycle-dependent conditions include abnormal cellular growth as found in neoplastic conditions, as well as biochemical processes relevant to arthritis, pain, inflammation, and platelet aggregation. See Y. Nishizuka, Science, 225, 1365-1370 (1984); S. K. Fisher and B. W. Agranoff, J. Neurochem., 48, 999-1017 (1987); Y. Sugimoto and R. I. Erikson, Molecular and Cellular Biology,5 3194-3198 (1985); K. Fukami, K. Matsuoka, O. Nakanishi, A. Yamakawa, S. Kawai, and T. Takenawa, Proc. Natl. Acad. Sci., U.S.A., 85, 9057-9061 (1988); M. Whitman, L. Fleischman, S. B. Chahwala, L. Cantley, and P. Rosoff, in Phosphoinositides and Receptor Mechanisms, 195-217, A. R. Liss, Inc. 1986.

4.2. Compounds of the Present Invention

The present invention also provides compounds represented by the formula II:

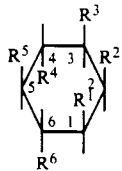

II wherein:

$R^1$, $R^2$, $R^3$, $R^4$, $R^5$ and $R^6$ is each independently selected from the group consisting of OH, F, $N_3$, $NH_2$, SH, SeH, Cl, Br, I and CN; with the proviso:

(i) four or five of said $R^1$, $R^2$, $R^3$, $R^4$, $R^5$ and $R^6$ are OH;

(ii) if one of said $R^1$, $R^2$, $R^3$, $R^4$, $R^5$ and $R^6$ is $N_3$, then one of said $R^1$, $R^2$, $R^3$, $R^4$, $R^5$ and $R^6$ is selected from the group consisting of F, $NH_2$, SH, SeH, Cl, Br, I and CN;

(iii) if one of said $R^1$, $R^2$, $R^3$, $R^4$, $R^5$ and $R^6$ is $NH_2$, then one of said $R^1$, $R^2$, $R^3$, $R^4$, $R^5$ and $R^6$ is selected from the group consisting of F, $N_3$, SH, SeH, Cl, Br, I and CN; and (iv) if said $R^4$, $R^5$ or $R^6$ is F, Cl, Br or I then four of said $R^1$, $R^2$, $R^3$, $R^4$, $R^5$ and $R^6$ are OH.

The preferred compounds of formula II are wherein five of said $R^1$, $R^2$, $R^3$, $R^4$, $R^5$ and $R^6$ are OH, i.e. monosubstituted compounds, and one of said $R^1$, $R^2$, $R^3$, $R^4$, $R^5$ and $R^6$, and more preferably said $R^1$, is selected from the group consisting of F, SH, SeH, Cl, Br, I and CN. However, due to that the 3-position substitution is very easy to synthesize, another preferred embodiment of the present invention is wherein said $R^1$, $R^2$, $R^4$, $R^5$ and $R^6$ is OH and $R^3$ is selected from the group consisting of F, SH, SeH, Cl, Br, I and CN.

Of the non-OH substituents, F and SH are preferred, with F most preferred.

A less preferred embodiment of formula II is wherein four of said $R^1$, $R^2$, $R^3$, $R^4$, $R^5$ and $R^6$ are OH and two of said $R^1$, $R^2$, $R^3$, $R^4$, $R^5$ and $R^6$ are selected from the group consisting of F, $N_3$, $NH_2$, SH, SeH, Cl, Br, I and CN, i.e. disubstituted compounds. Of such disubstituted compounds, it is preferred that two of said $R^1$, $R^4$ and $R^5$, yet more preferably said $R^4$ and $R^5$ be independently selected from the group consisting of F, $N_3$, $NH_2$, SH, SeH, Cl, Br, I and CN.

Of the non-OH substituents of the disubstituted compounds, preferred are F and SH; F and $NH_2$; $NH_2$ and SH; SH and SH; and F and F; with F and F being most preferred.

The preferred compounds of formula II are also the preferred compounds for use in the methods of the present invention.

4.3. Mode of Administration and Pharmaceutical Compositions

When the compounds of formula I are utilized in vivo, such compounds can be administered orally, topically, parentally, by inhalation spray or rectally in dosage unit formulations containing conventional non-toxic pharmaceutically acceptable carriers.

Accordingly, the present invention also provides pharmaceutical compositions comprising the compounds of formula II with a pharmaceutically acceptable carrier.

The term parenteral as used herein includes subcutaneous injections, intravenous, intramuscular, intrasternal injection or infusion techniques In addition to the treatment of mammals, such as mice, rats, horses, dogs, cats, etc., the compounds of the invention are effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparation.

Formulations for oral use include tablets which contain the active ingredient in admixture with non-toxic pharmaceutically acceptable excipients. These excipients may be, for example, inert diluents, such as calcium carbonate, sodium carbonate, lactose, calcium phosphate or sodium phosphate, granulating and disintegrating agents, for example, maize starch, or alginic acid; binding agents, for example, starch, gelatin or acacia, and lubricating agents, for example, magnesium stearate, stearic acid or talc. The tables may be uncoated or they may be coated by known techniques to delay disintegration and absorption in the gastrointestinal tract and thereby provide a sustained action over a longer period. For example, a time delay material such as glyceryl monostearate or glyceryl disterate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin, or olive oil.

Aqueous suspensions usually contain the active materials in admixture with appropriate excipients Such excipients are suspending agents, for example, sodium carboxymethylcellulose, methylcellulose, hydroxypropylmethylcellulose, sodium alinate, polyvinylpyrrolidone, gum tragacanth and gum acacia; dispersing or wetting agents which may be a naturally-occurring phosphatide, for example, lecithin; a condensation product of an alkylene oxide with a fatty oxide, for example, polyoxyethylene stearate; a condensation product of ethylene oxide with a long chain aliphatic alcohol, for example, heptadecaethyleneoxycetanol; a condensation product of ethylene oxide with a partial ester derived from fatty acids and a hexitol such as polyoxyethylene sorbitol monooleate; or a condensation product of ethylene oxide with a partial ester derived from fatty acids and hexitol anhydrides, for example, polyoxyethylene sorbitan monooleate. The aqueous suspensions may also contain one or more preservatives, for example, ethyl, n-propyl, or p-hydroxybenzoate; one or more coloring agents; one or more flavoring agents; and one or more sweetening agents such as sucrose or saccharin.

Oily suspension may be formulated by suspending the active ingredients in a vegetable oil, for example, arachis oil, olive oil, sesame oil or coconut oil, or in a mineral oil such as liquid paraffin. The oily suspension may contain a thickening agent, for example, beeswax, hard paraffin or cetyl alcohol. Sweetening agents such as those set forth above, and flavoring agents may be added to provide a palatable oral preparation. These compositions may be preserved by the addition of an antioxidant such as ascorbic acid.

Dispersible powders and granules suitable for preparation of an aqueous suspension by the addition of water provide the active ingredient in admixture with a dispersing or wetting agent, suspending and one or more preservatives. Suitable dispersing or wetting agents and suspending agents are exemplified by those already mentioned above. Additional excipients, for example, sweetening, flavoring and coloring agents, may also be present.

The pharmaceutical compositions of the invention may also be in the form of oil-in-water emulsions. The oily phase may be a vegetable oil, for example, olive oil or arachis oils, or a mineral oil, for example, liquid paraffin or mixtures of those. Suitable emulsifying agents may be naturally-occurring gums, for example, gum acacia or gum tragacanth, naturally-occurring phosphatides, for example, soybean lecithin; and esters including partial esters derived from fatty acids and hexitol anhydrides, for example, sorbitan mono-oleate, and condensation products of said partial esters with ethylene oxide, for example, polyoxyethylene sorbitan mono-oleate. The emulsions may also contain sweetening and flavoring agents.

Syrups and elixirs may be formulated with sweetening agents, for example glycerol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may be a sterile injectable solution or suspension in a non-toxic parenterally-acceptable diluent or solvent. Among the acceptable vehicles and solvents that may be employed are water, 1,3-butanediol, Ringer's solution and isotonic sodium chloride solution. In addition, sterile fixed oils are conventionally employed as a solvent or suspending medium. For this purpose any bland fixed oil may be employed including synthetic mono- or diglycerides. Fatty acids such as oleic acid also find use in the preparation of injectables.

The compounds of formula I can also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug, for example, cocoa butter and polyethylene glycols.

When the compounds of formula I are utilized in vivo, dosage levels on the order of from about 0.2 mg to about 300 mg, preferably from about 10 mg to about 100 mg, per kilogram of body weight per day are useful.

5. EXAMPLES

5.1. Synthesis of Compounds of Formula I

EXAMPLE I

Synthesis of 3-deoxy-3-fluoro-myo-inositol and 1-deoxy-1-fluoro-myo-inositol

The following synthesis is with reference to the scheme set forth in Scheme 1 hereinbelow. (The number after the compounds referred to in this scheme refer to the compounds designated by the same number in Scheme 1. Also, some compounds referred to in the scheme are only referred to by the number, which also refers to the compound in Scheme I designated by such number. The subsequent examples are written in the same manner.)

Preparation of Monocyclohexylidene Ketal 2

A 2-L flask equipped with a mechanical stirrer, a Dean-Stark trap and a reflux condenser was charged with myo-inositol (50 g), cyclohexanone (500 mL), and anhydrous benzene (130 mL). The mixture was stirred and refluxed until no more water separated. $p$-Toluensulphonic acid monohydrate (p-TsOH) (0.5 g) was added and the mixture was refluxed until the separation of water was complete and almost all the myo-inositol had dissolved (about 4 hr.). The mixture was cooled and decanted from the remaining solid, which was washed with 50 mL of benzene. More benzene (200 mL), light petroleum (b.p. 60°-80°) (250 mL), and ethanol (50 mL) were added in this order to the solution. The solution was kept at 0° C. overnight. Triethylamine (1 mL) was added and the solid was filtered and washed with benzene The crude product was purified by extraction with boiling ethanol (1000 mL) containing triethylamine (1 mL). On cooling, the product (ca 54 g. 74%) crystallized.

Preparation of Diol 3

A mixture of the monocyclohexylidine ketal 2 (36.8 g, 0.142 mol), benzyl chloride (407 g, 3.21 mol), and potassium hydroxide (220 g, 3.93 mol) was stirrred with a mechanical stirrer at 90°-100° C. for 20 hours. The cooled mixture was diluted with benzene (400 mL) and washed with water (4×150 mL). The benzene solution was concentrated on a rotary evaporator, and the residue was heated in glacial acetic acid (800 mL) and water (160 mL) at 90°-100° C. for 4 hours. The solution was concentrated on a rotary evaporator at 55° C. and the residue was purified by column chromatography (30% ethyl acetate in hexanes than 40% ethyl acetate in hexanes); yield 36 g (42%) of 3.

Preparation of Monobenzoyl Ester 4

Benzoyl chloride (1.1 mol. equiv.) was added dropwise to a solution of the diol 3 (1 g) in pyridine (50 mL). The solution was stirred at room temperature for 4 hours. The pyridine was evaporated and the residue was taken up in ethyl acetate and washed with water. After drying and concentration, the crude product was purified by flash chromatography (40% ethyl acetate in hexanes); yield 80%.

Fluorination of Monobenzoyl Ester 4

To a solution of the monobenzoyl ester 4 in toluene at 80° C. was added dropwise diethylamino-sulfur trifluoride (DAST) (2 mol equiv.). The solution was kept at 80° C. for 1 hour. After cooling down to room temperature, the solution was diluted with benzene and washed with brine. The solution was dried over $MgSO_4$, filtered, and concentrated. Flash chromatography (20% ethyl acetate in hexanes) gave the pure product 5 in 76% yield.

Preparation of Racemic Equatorial Alcohol 6

Methanol was added to a mixture of the fluorinated monobenzoyl ester 5 (0.37 g, 0.58 nmol) in 5% NaOH-THF (1:1, 40 mL) until the mixture became homogeneous. The solution was stirred at room temperature for 1 hour. Methanol and THF were removed by a rotary evaporator. The aqueous layer was extracted with ethyl acetate. The extracts were washed with brine, dried, and concentrated. Flash chromatography (20% ethyl acetate in hexanes) gave 0.23 g of racemic alcohol 6 (73%).

Preparation of (−) and (+) Diastereomeric Camphanic Esters [(−) and (+) 7, respectively]

(S)-(−)-camphanic acid chloride (1.11 g, 2 mol equiv.) was added in several portions quickly to a solution of racemic alcohol 6 (1.38 g, 2.55 mmol), triethylamine (1.76 mL, 5 mol equiv.), and a catalytic amount of 4-dimethylaminopyridine (DMAP) in dry dichloromethane (50 mL) at room temperature. The solution was stirred at room temperature for 2 hours. The solution was then diluted with dichloromethane, washed with saturated $NH_4Cl$, dried and concentrated. Flash chromatography (FC) (20% ethyl acetate in hexanes, 100 g of 230–400 mesh silica gel per gram of crude product) separated the two diastereomeric camphanic esters with the less polar one being the (−) camphanic ester 7 (3-fluoro-) and the more polar one being the (+) camphanic ester 7 (1-fluoro-). The combined yield was approximately 90%.

Hydrolysis of the (−)-Camphanic Ester 7

Methanol was added to a mixture of the (−)-camphanic ester 7 (332 mg, 0.460 nmol) in 1:1 5% NaOH—THF (60 mL) at room temperature until the mixture became homogeneous. Stirring was continued at room temperature for 2 hours. MeOH and THF were evaporated on a rotavap. The resulting aqueous mixture was extracted with AcOEt. The organic phase was washed with brine, dried and concentrated Flash chromatography (20% ethyl acetate in hexanes) gave the (+)-alcohol 8 (237 mg. 95%).

Oxidation of (+)-Alcohol 8

To a solution of oxalyl chloride (3 mol equiv.) in dry $CH_2Cl_2$ at −78° C. under $N_2$ was added dimethylsulfoxide (DMSO) (7 mol equiv.). After stirring at −78° C. for 15 minutes, a solution of the (+)-alcohol 8 in dichloromethane (1 g in 5 mL) was introduced dropwise through a syringe. Stirring was continued at −78° C. for 1 hour. Triethylamine (10 mol equiv.) was added and the resulting solution was allowed to warm up slowly to room temperature. Water was added to the solution and volatile organics were evaporated on a rotary evaporator. The resulting aqueous mixture was extracted with AcOEt. The organic phase was washed with water (3 times) and brine, dried and concentrated. The ketone 9 (ca. 80%) was used directly for the next step.

Reduction of Ketone 9

To a solution of the ketone 9 (0.826 g, 1.532 mmol) in dry THF (50 mL) at −78° C. under $N_2$ was added dropwise L-Selectride (2.30 mL of a 1M solution in THF, 1.5 mol equiv.). The solution was warmed slowly to room temperature. Saturated $NH_4Cl$ was added to quench the excess reagent. THF was evaporated and the aqueous mixture was extracted with AcOEt. The organic layer was washed with brine, dried and concentrated. Flash chromatography (20% ethyl acetate in hexanes) gave the (+)-axial alcohol 10 (0.669 g, 81%).

Hydrogenolysis of the (+)-Axial Alcohol 10

A mixture of the (+)-axial alcohol 10 (177 mg.), several drops of 5% HCl, and 10% Pd/C (equal weight with the axial alcohol(+)-10) in EtOH (30 mL) was stirred under an atmosphere of $H_2$ at room temperature overnight. The catalyst was filtered, and the filtrate was concentrated first on a rotary evaporator and then by high vacuum to yield (greater than 95% yield) 3-deoxy-3-fluoro-myo-inositol. Recrystallization from methanol gave crystalline 3-deoxy-3-fluoro-myo-inositol.

The same chemical synthesis can be utilized to prepare 1-deoxy-1-fluoro-myo-inositol, which is the enantiomer of 3-deoxy-3-fluoro-myo-inositol, except that (−)8 compound rather than the (+)8 compound is utilized.

Scheme 1

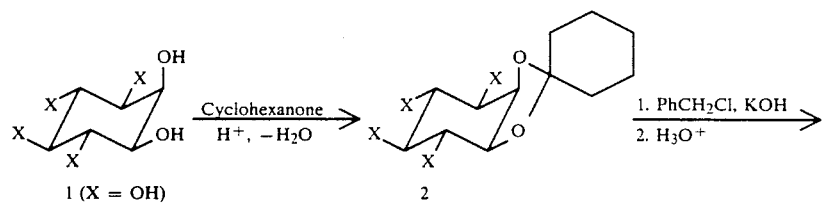

Scheme 1

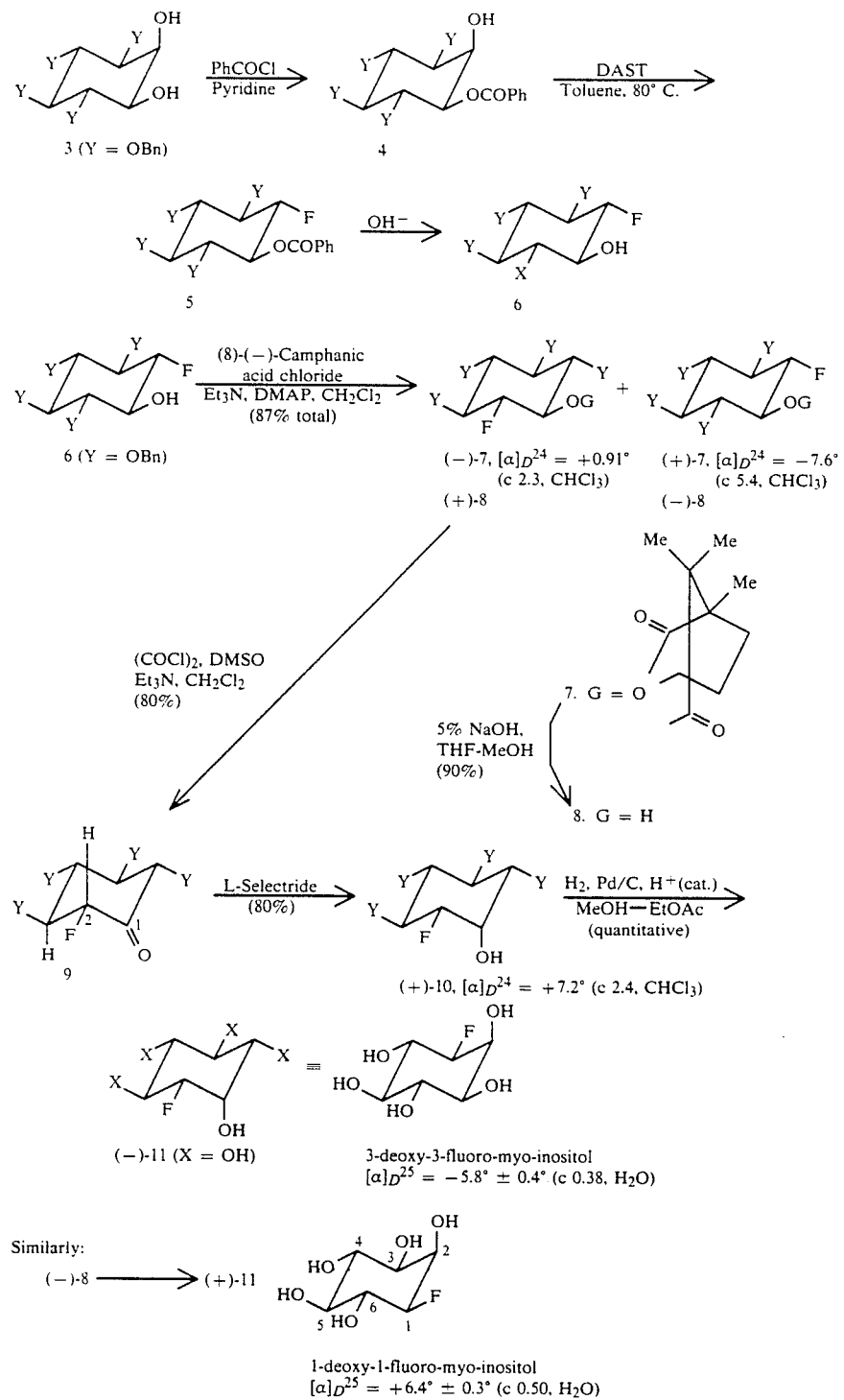

3-deoxy-3-fluoro-myo-inositol
$[\alpha]_D^{25} = -5.8° \pm 0.4°$ (c 0.38, H$_2$O)

Similarly:
(−)-8 ⟶ (+)-11

1-deoxy-1-fluoro-myo-inositol
$[\alpha]_D^{25} = +6.4° \pm 0.3°$ (c 0.50, H$_2$O)

The spectral data for the compounds of this example was as follows:

2: $^1$H NMR (D$_2$O): δ 4.45 (t, J=4.4 Hz, 1 H), 4.02 (dd, J=7.7, 5.1 Hz, 1 H), 3.82 (dd, J=9.7, 4.1 Hz, 1 H), 3.52–3.65 (m, 2 H), 3.23 (t, J=10.0 Hz, 1 H), 1.34–1.73 (m, 10 H).

3: R$_f$(40% ethyl acetate in hexanes)=0.22; $^1$H NMR: δ 7.23–7.30 (m, 20 H), 4.69–4.94 (m, 8 H), 4.17 (br s, 1 H), 3.96 (t, J=9.4 Hz, 1 H), 3.82 (t, J=9.4 Hz, 1 H), 3.42–3.49 (m, 3 H), 2.53 (br s, —OH), 2.44 (br d, J=3.8 Hz, —OH).

4: R$_f$(40% ethyl acetate in hexanes)=0.67; $^1$H NMR: δ 7.13–8.18 (m, 25 H), 5.11 (br d, J=10.2 Hz, 1 H), 4.70–4.94 (m, 8 H), 4.42 (br s, 1 H), 4.24 (t, J=9.4 Hz, 1 H), 4.02 (t, J=9.4 Hz, 1 H), 3.58–3.64 (m, 2 H), 2.54 (br s, —OH).

5: R$_f$(20% ethyl acetate in hexanes)=0.37; $^1$H NMR: δ 7.05–8.04 (m, 25 H), 5.53 (dt, J=12.1, 9.7 Hz, H), 4.62–4.93 (m, 8 H), 4.61 (dt, J=51, 9.5 Hz, 1 H), 3.80 (dt, J=12.7, 9.2 Hz, 1 H), 3.57–3.75 (m, 3 H).

6: $R_f$(20% ethyl acetate in hexanes)=0.15; $^1$H NMR: δ 7.24–7.37 (m, 20 H), 4.74–4.95 (m, 8 H) 4.42 (dt, J=51, 8.9 Hz, 1 H), 3.51–3.78 (m, 4 H), 3.39 (t, J=9.0 Hz, 1 H), 2.49 (d, J=2 Hz, —OH).

(−)-7: white solid, mp=136°–138° C.;

$R_f$(20% ethyl acetate in hexanes)=0.22;

IR: 3063, 3031, 2967, 2933, 2878, 1791, 1741, 1496, 1453, 1397, 1360, 1337, 1315, 1271, 1212, 1163, 1141, 1098, 1061, 1028, 993, 930, 736, 698 cm$^{-1}$;

$^1$H NMR: δ 7.22–7.33 (m, 20 H), 5.34–5.43 (m, 1 H), 4.68–4.90 (m, 8 H), 4.54 (dt, J=51, 9.3 Hz, 1 H), 3.52–3.79 (m, 4 H), 2.36–2.45 (m, 1 H), 1.73–1.94 (m, 2 H), 1.56–1.67 (m, 1 H), 1.11 (s, 3 H), 1.04 (s, 3 H), 0.99 (s, 3 H);

Mass spectrum (m/z): 631 (M$^+$—91), 525, 433, 327, 299, 197, 181, 91, 55, exact mass calcd for $C_{37}H_{40}FO_8$ 631.2707, found 631.2705; Anal. Calcd for $C_{44}H_{47}FO_8$: C, 73.11; H, 6.55; F, 2.63, found: C, 72.94; H, 6.33; F, 2.49;

$[α]_D^{24}$=7.6° (c 5.4, CHCl$_3$).

(+)-7: glassy solid;

$R_f$(20% ethyl acetate in hexanes)=0.16;

IR: 3062, 3031, 2965, 2932, 2879, 1792, 1761, 1497, 1453, 1397, 1360, 1333, 1310, 1264, 1214, 1142, 1061, 1028, 933, 736, 698 cm$^{-1}$;

$^1$H NMR: δ 7.18–7.32 (m, 20 H), 5.42 (dt, J=11, 9.7 Hz, 1 H), 4.64–4.91 (m, 8 H), 4.51 (dt, J−51, 9.4 Hz, 1 H), 3.52–3.80 (m, 4 H), 2.30–2.40 (m, 1 H), 1.85–2.00 (m, 2 H), 1.63–1.72 (m, 1 H), 1.09 (s, 3 H), 1.05 (s, 3 H), 0.88 (s, 3 H);

Mass spectrum (m/z): 631 (M$^+$—91), 525, 433, 327, 299, 197, 181, 91; exact mass calcd for $C_{37}H_{40}FO_8$ 631.2707, found 631.2705; Anal. Calcd for $C_{44}H_{47}FO_8$: C, 73.11; H, 6.55; F, 2.63, found: C, 72.77; H, 6.51; F, 2.49;

$[α]_D^{24}$= +0.91° (c 2.3, CHCl$_3$).

(+)-8 (derived by hydrolysis of (−)-7): white solid, mp=121°–123° C.

$R_f$(20% ethyl acetate in hexanes)=0.15;

IR: 3285 (br), 3030, 2924, 1496, 1468, 1452, 1402, 1358, 1215, 1134, 1103, 1066, 1043, 1022, 904, 738, 694, 661, 630 cm$^{-1}$;

$^1$H NMR: δ 7.24–7.37 (m, 20 H), 4.74–4.95 (m, 8 H) 4.42 (dt, J=51, 8.9 Hz, 1 H), 3.51–3.78 (m, 4 H), 3.39 (t, J=9.0 Hz, 1 H), 2.49 (d, J=2 Hz, —OH);

Mass spectrum (m/z): 451 (M$^+$—91), 363, 253, 197, 181, 91; exact mass calcd for $C_{27}H_{28}FO_5$ 451.1921, found 451.1920;

Anal. Calcd for $C_{34}H_{35}FO_5$: C, 75.25; H, 6.50; F, 3.50, found: C, 75.19; H, 6.47, F, 3.44;

$[α]_D^{25}$= +7.2° (c 1.7, CHCl$_3$).

(−)-8 (derived by hydrolysis of (+)-7): $[α]_D^{25}$= +7.2° (c 1.7, CHCl$_3$).

Ketone 9: white solid;

IR: 3063, 3030, 2872, 1740, 1496, 1454, 1358, 1213; 1140, 1068, 1026, 972, 735, 696 cm$^{-1}$;

$^1$H NMR: δ 7.22–7.39 (m, 20 H), 5.04 (ddd, J=49, 9.8, 1.4 Hz, 1 H), 4.50–4.92 (m, 8 H), 4.19 (dd, J=9.8, 1.2 Hz, 1 H), 3.86 (t, J=9.2 Hz, 1 H), 3.71 (dt, J=13, 9.5 Hz, 1 H), 3.65 (t, J=9.4 Hz, 1 H);

Mass spectrum (m/z): 449 (M+91), 341, 181, 91, exact mass calcd for $C_{24}H_{26}O_5F$ 449.1764, found 449.1763;

Since ketone 9 is not completely homogeneous from NMR analysis, no mp or optical rotations were measured for either enantiomer.

(+)-10 (derived from (+)-8): Colorless oil;

$R_f$(20% ethyl acetate in hexanes)=0.13;

IR: 3453 (br), 3065, 3032, 2924, 1496, 1454, 1361, 1211, 1153, 1070, 1028, 733, 696 cm$^{-1}$;

$^1$H NMR: δ 7.27–7.33 (m, 20 H), 4.64–4.90 (m, 8 H), 4.42 (ddd J=44, 9.6, 2.5 Hz, 1 H), 4.33 (br s, 1 H), 4.15 (dt, J=11, 9.5 Hz, 1 H), 3.98 (t, J=9.6 Hz, 1 H), 3.41–3.47 (m, 2H), 2.49 (s, —OH);

Mass spectrum (m/z): 451 (M$^+$—91), 253, 197, 181, 91, exact mass calcd for $C_{27}H_{28}FO_5$, 451.1921, found 451.1920;

Anal. Calcd for C, 75.25; H, 6.50; F, 3.50, found: C, 75.47; H, 6.49; F, 3.39;

$[α]_D^{24}$= +7.2° (c 2.4, CHCl$_3$).

(−)-10 (derived from (−)-8): $[α]_D^{24}$= +7.2° (c 1.2, CHCl$_3$).

3-deoxy-3-fluoro-myo-inositol (derived from (+)-10): m.p.=dec. 200° C.;

IR: 3337 (br), 2926, 1107, 1034 cm$^{-1}$;

$^1$H NMR (300 MHz, D$_2$O): δ 4.43 (DDD, J=47, 9.8, 2.9 Hz, 1 H) 4.27 (dt, J=8.2, 2.9 Hz, 1H), 3.88 (dt, J=11, 9.5 Hz, 1 H), 3.63 (t, J=9.6 Hz, 1 H), 3.52 (ddd, J=9.9, 2.6, 1.1 Hz, 1 H), 3.27 (t, J=9.5 Hz, 1 H);

Mass spectrum (m/z): 181 (M$^+$ −1), 149, 132, 119, 57, 43;

$[α]_D^{25}$= −5.8°±(c 0.38, H$_2$O).

EXAMPLE II

Synthesis of 3-deoxy-3-fluoro-myo-inositol

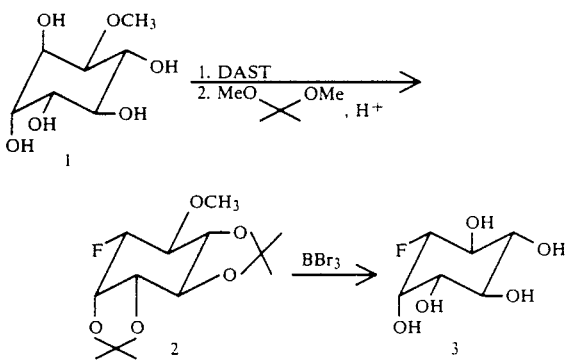

Quebrachitol 1, which is extracted from waste-solids of rubber serum, is commercially available from the Rubber Research Institute of Malaysia. (0.173 g, 0.95 mmol, crystallized from methanol/acetone) was mixed with diethylaminosulfur trifluoride (DAST, 600 L, 5.75 mmol) at 0° C. and the resulting mixture, after stirring at room temperature under argon for 1.5 h, was cooled to −40° C. Methanol (2 mL) was added dropwise (caution). Methanol was evaporated at reduced pressure and a light brown residue was obtained, which is the fluorinated compound. Such compound was dissolved in 32 mL of dry DMF and 2 mL of 2,2-dimethoxypropane along with 20 mg of p-TsOH, this step is optional and is utilized to protect the free hydroxy groups. The mixture was heated under argon at 40° C. for 12 h. Saturated aqueous, sodium bicarbonate solution (10 mL) and water (50 mL) were added, and the mixture was extracted with 4×50 ml portions of ether. The ethereal extracts were combined, washed with water and brine, and dried (MgSO$_4$). Evaporation under reduced pressure furnished an oily residue which was purified by column chromatography on silica gel using 20% (v/v) EtOAc/hexane as eluant to give fluorodiacetonide 2 as an oil. Rf 0.25 1:5 EtOAc/hexane. $^1$H NMR (CDCl$_3$), 300 (MHz) δ 4.6 (br, d, J=47.2 Hz, 1 H), 4.32 (m, 1 H), 4.19 (dd, J=7.3, 7.3 Hz, 1 H) 3.98 (ddd, J=31.7, 7.3, 2.6 Hz), 3.7 (br dd, J=19.2, 7.6 Hz), 3.34 (dd, J=0.8, 7.6 Hz), 3.11 (s, 3 H), 1.55 (s, 3 H), 1.34 (s, 3 H), 1.22 (s, 3 H), 1.19 (s, 3 H).

The fluorodiacetonide 2 (40 mg, 0.15 mmol) was dissolved in 4 mL of methylene chloride and the mixture was cooled to 0° C. Neat boron tribromide (200 μL, 12 equiv.) was added via syringe. After stirring for 20 h. at room temperature, the mixture was subjected to rotary evaporation. MeOH (4 mL) was cautiously added at 0° C. and was evaporated at reduced pressure. The addition and evaporation of MeOH at reduced pressure was carried out several times. Water was added and the brown aqueous solution was exhaustively washed with CH₂Cl₂ to remove impurities. The aqueous phase was evaporated under reduced pressure to give 3-deoxy-3-fluoro-myo-inositol 3 as a pale yellow solid which was crystallized from MeOH. Yield=26.6 mg, 95%. The product was spectroscopically identical to the one synthesized in EXAMPLE I.

EXAMPLE III

Synthesis of 3-deoxy-3-mercapto-myo-inositol

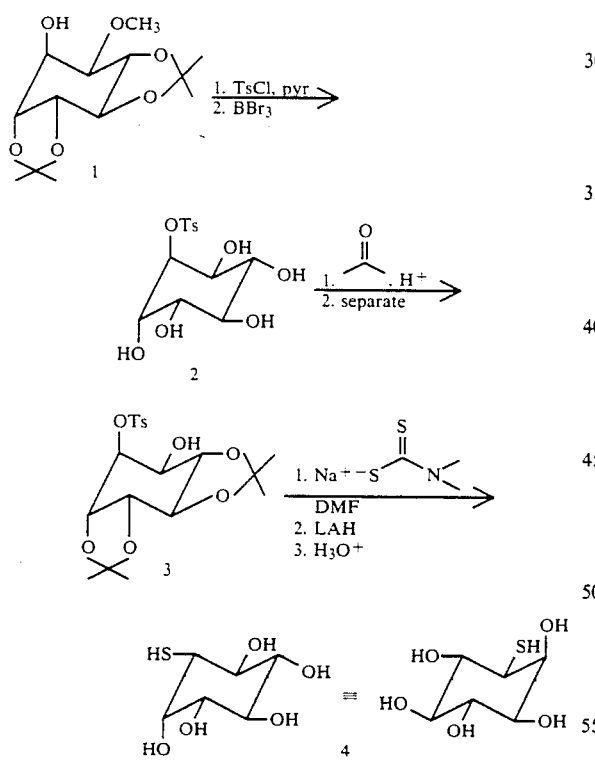

Quebrachitol diacetonide 1, which is prepared from quebrachitol by treatment with 2-methoxypropene and an acid, is tosylated and then treated with BBr₃ to provide the deprotected compound 2, which is converted to a mixture of bis-acetonides, which are separated by column chromatography to provide pure 3. Tosylate 3 is reacted sequentially with the sodium salt of dimethyldithiocarbamic acid in DMF, then with lithium aluminum hydride and finally with aqueous acid to provide the optically pure 3-deoxy-3-mercapto-myo-inositol 4.

EXAMPLE IV

Synthesis of 3,4-dideoxy-3,4-difluoro-myo-inositol

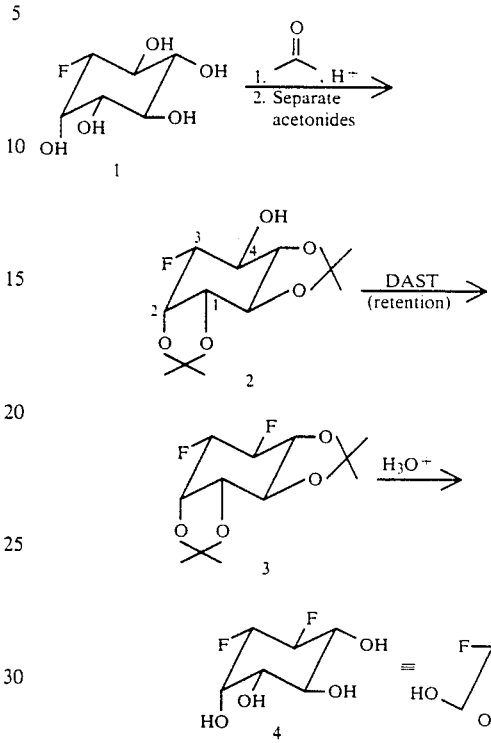

The 3,4-difluoro isostere of myp-inositol is prepared from the 3-fluoro-3-deoxy analog 1. Compound 1 is protected as its bisacetonide derivative, the acetonide mixture separated by chromatography, and compound 2 having a free C-4 hydroxyl group is treated with DAST. The isomer 3 of retained stereochemistry is then simply deprotected by aqueous acid treatment to provide the title compound 4.

EXAMPLE V

Synthesis of 3,4-dideoxy-3-azido-4-fluoro-myo-inositol

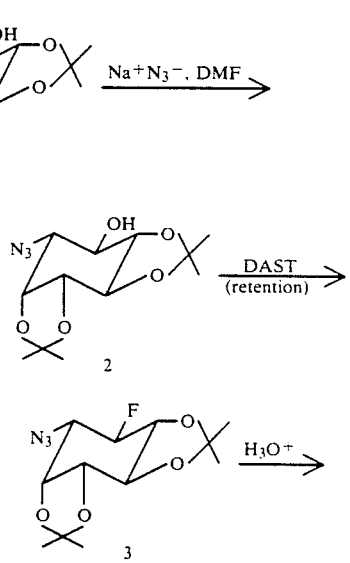

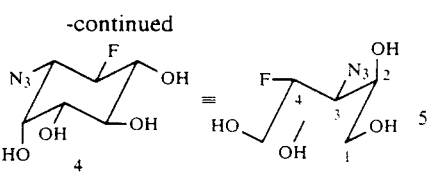

The previously described tosylate 1 is reacted with sodium azide in DMF to provide the protected azide 2. Next, DAST treatment of 2 provides the fluorine containing isomer 3 of retained stereochemistry. Cleavage of the acetonide protecting groups then affords the desired amino, fluoro containing isostere 4 of myo-inositol.

EXAMPLE IV

Synthesis of 3,4-dideoxy-4-fluoro-mercapto-myo-inositol

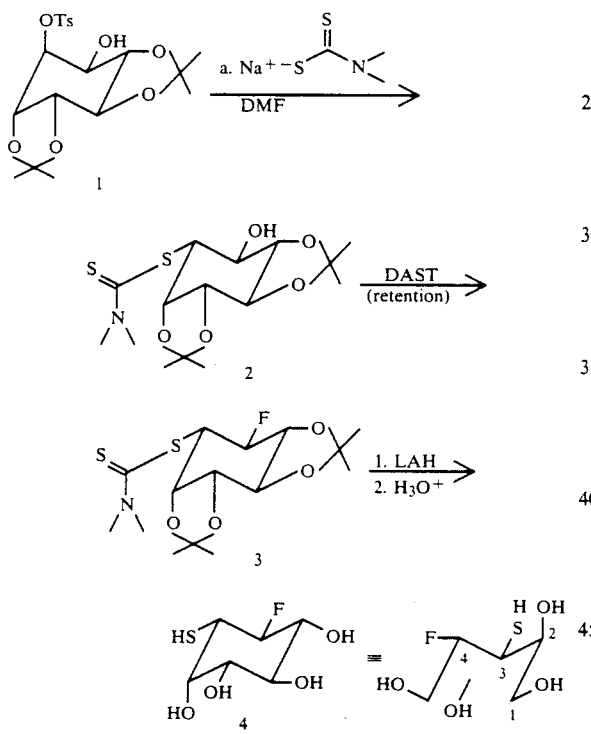

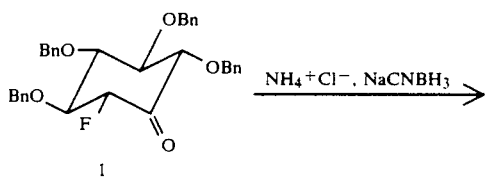

The previously described tosylate 1 is reacted with the sodium salt of dimethyldithiocarbamic acid in DMF to give 2. DAST treatment of 2 then provides 3 as the major fluorinated product. Lastly, treatment with lithium aluminum hydride and acid catalyzed removal of the acetonide groups yield the mercapto compound 4.

EXAMPLE VII

Synthesis of 2,3-dideoxy-2-amino-3-fluoro-myo-inositol

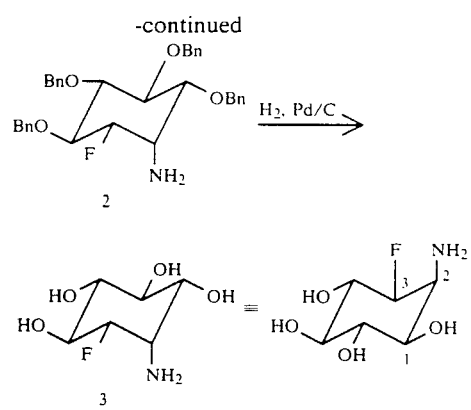

The previously described ketone 1 is subjected to a reductive amination procedure to afford the axial amine 2. The benzyl groups are then removed by catalytic hydrogenolysis to yield the title compound 3.

EXAMPLE VIII

Synthesis of 3,6-dideoxy-3,6-difluoro-myo-inositol

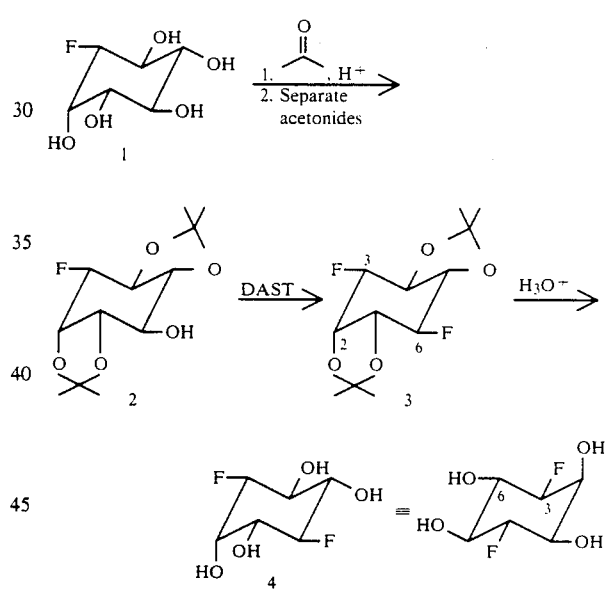

The previously described 3-fluoro-3-deoxy isostere 1 is protected as its bis-acetonide and the mixture of resulting acetonides separated to provide 2. DAST treatment of 2 provides some of the 6-fluoro product 3 of retained stereochemistry. The difluoro isostere 4 is then obtained by aqueous acid treatment of 3.

EXAMPLE IX

Synthesis of 3-deoxy-3-cyano-myo-inositol

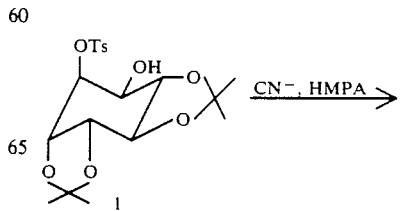

EXAMPLE XI

Synthesis of 2,3-dideoxy-2,3-difluoro myo-inositol

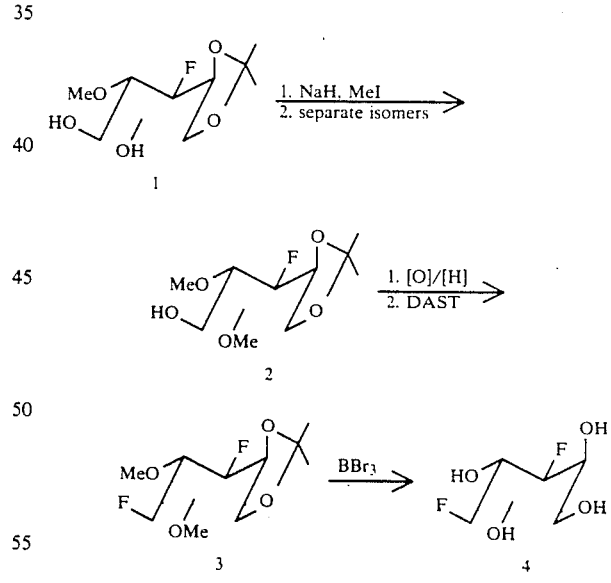

The C-1 equatorial hydroxyl group of the previously described intermediate 1 is protected by benzylation, and the axial C-2 hydroxyl group is inverted by an oxidation/reduction sequence. DAST treatment of this new intermediate 2, followed by deprotection of the hydroxyl groups completes the synthesis.

EXAMPLE XII

Synthesis of 3,5-dideoxy-3,5-difluoro-myo-inositol

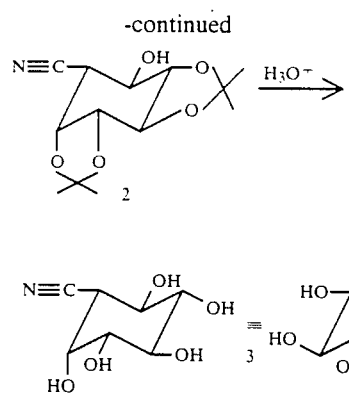

The previously described tosylate 1 is reacted with sodium cyanide in HMPA to provide the S$_N$2 displacement product 2. Acetonide removal is brought about by reaction with aqueous acid to yield the title compound 3.

EXAMPLE X

Synthesis of 1,3-Dideoxy-1,3-difluoro-myo-inositol

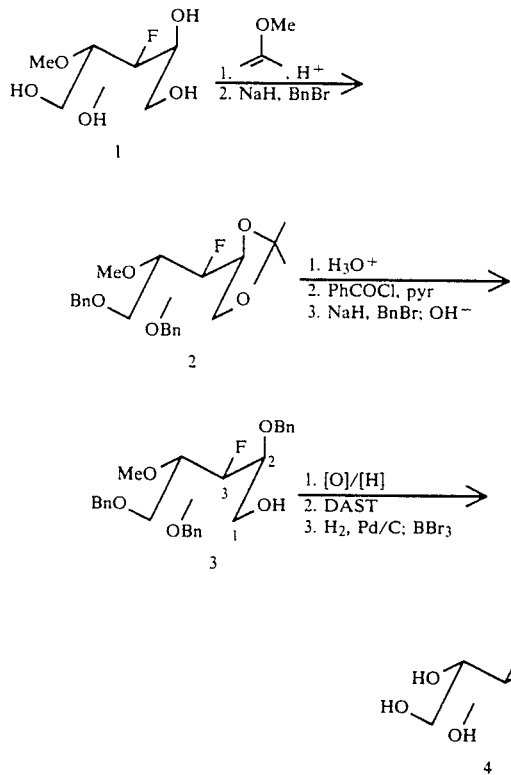

The previously prepared compound 1 is fully protected as 2, then selectively deprotected to provide 3. The free C-1 hydroxyl group is inverted by an oxidation/reduction sequence, and then transformed to a fluoro group by DAST treatment. A final deprotection step then affords the desired 1,3-difluoro isostere.

The previously described 3-deoxy-3-fluoro-myo-inositol is protected as its mono-acetonide derivative 1, and 1 is reacted with sodium hydride and methyl iodide to provide 2 after chromatographic purification. The C-5 hydroxyl group of 2 is inverted by an oxidation/reduction sequence, and this new alcohol is treated with DAST to yield 3. Lastly, deprotection with boron tribromide is carried out to give this title compound 4.

In a fashion identical to that described hereinabove for the preparation of the 1,3-difluoro analogs of myo-inositol, it is possible to replace any one of the hydroxy groups of 3-deoxy-3-fluoro-myo-inositol by an amino, azido, cyano, mercapto, fluoro, chloro, bromo, iodo or selenol group to afford a dideoxyinositol isostere. The strategy requires that all hydroxy groups except the one to be substituted be protected. Next, the remaining, free hydroxy group is inverted, then activated for displacement (e.g., by tosylate or mesylate formation), and a displacement reaction carried out using the appropriate halogen, carbon, nitrogen, sulfur, or selenium nucleophile. In some situations, inversion of the free alcohol may not be necessary, for the subsequent displacement reaction can proceed with retention of stereochemistry (e.g. introduction of a chlorine atom using thionyl chloride). Also, a reductive amination process can be used to introduce an amino group into the protected 3-deoxy-3-fluoro-myo-inositol derivative by oxidation of its free hydroxyl group to ketone, followed by imine formation and reduction. The desired disubstituted myo-inositol analog is then obtained by removal of all protecting groups.

In a similar fashion, by starting with any of the monosubstituted myo-inositol analogs containing a cyano, mercapto, selenol, fluoro, amino, chloro, bromo, iodo or azido group, and protecting all hydroxyl groups (as well as the non-hydroxyl functional group if necessary) except the one to be substituted, all other dideoxy-disubstituted analogs of myo-inositol can be generated. The free hydroxyl group is inverted, activated for displacement, and displaced using the appropriate nucleophile as described hereinabove. In some situations, inversion of the free alcohol group may not be necessary, for the subsequent displacement reaction can proceed with retention of stereochemistry. Also, the amino group can be advantageously introduced in certain cases by use of the reductive amination procedure. Lastly, deprotection of all functional groups delivers the required dideoxy-disubstituted inositol.

5.2 Biological Data

EXAMPLE XIII

Cell Growth Inhibition Effects Of
3-deoxy-3-fluoro-myo-inositol and
1-deoxy-1-fluoro-myo-inositol The biological effects of the 3-fluoro and 1-fluoro-myo-inositol analogs were tested in PC12 cells, a cell line derived from a rat pheochromocytoma, which has been widely used to study the effects of various growth factors and differentiation promoters as further described by Green, L. A., et al., *Adv. Cell Neurobiol.*, 3, 373-414, (1982), the disclosure of which is incorporated herein by reference.

PC12 cells were seeded at a density of $3.3 \times 10^5$ cells/cm$^2$ in plastic culture dishes and grown at 37° C. in a humidified atmosphere of 95% air/5% $CO_2$. The basal medium used in these experiments was RPMI-1640 medium (Gibco). In some experiments a specially formulated inositol-free RPMI-1640 medium (Gibco) was used. This basal medium was supplemented with either normal or extensively dialyzed horse serum (10%) and fetal calf serum (5%) (Gibco). Some control dishes were grown in complete RPMI medium, i.e. with myo-inositol and containing non-dialyzed serum (Control 1) and some control dishes were grown in inositol deficient medium, i.e., RPMI without inositol and with dialyzed serum (Control 2). The inositol analogs were dissolved in distilled $H_2O$ and added to the culture medium at the indicated concentrations.

Cell counts were performed by removing the medium, washing the cells gently in PBS with calcium, detaching the cells by 15 minute induction in PBS/EDTA (0.5 mM) containing 0.1% trypsin, and counting in a hemocytometer.

A dose-response study was performed by growing cells in the presence of certain concentrations of the 3-fluoro and the 1-fluoro-myo-inositol analogs. At the end of five days, the cells were counted by the means described hereinabove. The results, shown in Table 1, were as follows:

TABLE 1

| Dose Response for Myo-Inositol Analogs | |
|---|---|
| Treatment | Cell Number ($\times 10^5$ cells/dish) |
| Control Medium | |
| 1 | 5.1 ± 0.2 |
| 2 | 4.7 ± 0.1 |
| 1-deoxy-1-fluoroinositol (mM) | |
| 0.01 | 4.53 ± 0.13 |
| 0.03 | 4.18 ± 0.07 |
| 0.10 | 3.71 ± 0.03 |
| 0.30 | 3.29 ± 0.08 |
| 1.0 | 2.73 ± 0.13 |
| 3.0 | 2.67 ± 0.09 |
| 10.0 | 2.68 ± 0.07 |
| 30.0 | 2.72 ± 0.03 |
| 3-deoxy-3-fluoroinositol (mM) | |
| 0.01 | 4.60 ± 0.24 |
| 0.03 | 4.49 ± 0.07 |
| 0.10 | 4.21 ± 0.05 |
| 0.30 | 3.87 ± 0.05 |
| 1.0 | 3.21 ± 0.08 |
| 3.0 | 2.53 ± 0.04 |
| 10.0 | 2.50 ± 0.03 |
| 30.0 | 2.36 ± 0.01 |

Thus, it can be seen that both analogs inhibited cell replication by approximately 50%, with the 1-deoxy-1-fluoro-myo-inositol analog being about five-fold more potent than the 3-deoxy-3-fluoro-myo-inositol analog.

The time course effect on cell replication was then examined, using the concentration of 1-fluoro and 3-fluoro myo-inositol analogs determined to have maximal effects in the dose response study of Table 1. (1 mM and 5 mM for the 1-fluoro and 3-fluoro-myo-inositol analogs, respectively). The results, shown in Table 2, were as follows:

TABLE 2

| | Time Course Cell Counts TREATMENT GROUP | | |
|---|---|---|---|
| Time | Control Medium 2 (Inositol Free) | 1-deoxy-1-Flouroinositol (1 mM) | 3-deoxy-3-Fluoroinositol (5 mM) |
| Day 0 | $1.46 \times 10^5$ | $1.46 \times 10^5$ | $1.46 \times 10^5$ |
| Day 1 | 2.52 ± 0.08 | 2.10 ± 0.03 | 2.12 ± 0.02 |
| Day 3 | 8.0 ± 0.3 | 4.5 ± 0.10 | 4.2 ± 0.1 |
| Day 5 | 16.6 ± 1.1 | 8.4 ± 0.7 | 7.6 ± 0.1 |
| Day 7 | 17.0 ± 0.5 | 10.8 ± 0.6 | 10.6 ± 0.6 |

Numbers represent cells per dish, $\times 10^5$.

Thus, since there was no decline in cell number over time, it is believed that the 50% decrease in cell number was the result of a persistent inhibition in cell replication, rather than a cytotoxic effect resulting in cell death. Furthermore, it is believed that such inhibition was not the result of simple inositol depletion caused by the blockade of myo-inositol transport into the cells by the myo-inositol analogs, since control cells grown in inositol-free, dialyzed serum (Control 2), grew almost as well as control cells grown in complete medium, i.e., myo-inositol containing medium, (Control 1), with both sets of control cultures demonstrating considerably faster replication than the fluoro-myo-inositol-treated cultures.

EXAMPLE XIV

Effects of Fluoroinositol Analogs on Cell Size

Background

As cells grow in culture, the size of an individual cell varies in a fairly predictable way. The size of a cell can be expressed as the amount of protein present per cell. Shortly before mitosis (i.e., cell division), a cell is at its largest diameter and, hence, possesses the greatest amount of protein per cell. Immediately after mitosis, the cell size drops considerably, frequently to levels approximately half of the pre-mitotic level.

By investigating the size of a cell, it is possible to determine at which point within the cell cycle inhibitors of cell replication are exerting their effects. Accordingly, we investigated the effect of the 1- and 3-fluoro-myo-inositol analogs on the size of cells chronically treated with such analogs.

Method

Cells were grown and treated with 1- and 3-fluoro-myo-inositol analogs as described in Example XIII. On the days indicated, cells were gently harvested without disruption, and the number of cells counted in triplicate in a cell counting chamber. Following determination of the number of cells per sample, the remainder of the cells were pelleted in a microcentrifuge as described hereinabove, and the protein in the sample was determined by the method of Lowry. Thus, it was possible to derive from these two data sets the amount of protein per cell, which is expressed as nanograms of protein per cell, as indicated in Table 3:

TABLE 3

Effects of Fluoroinositol Treatment on Cell Size

| Treatment Duration (Days) | Control 2 | 1-deoxy-1-Fluoroinositol (nanograms protein/cell) | 3-deoxy-3 Fluoro-inositol |
|---|---|---|---|
| 1 | 0.110 ± 0.01 | 0.082 ± 0.01 | 0.086 ± 0.01 |
| 3 | 0.118 ± 0.03 | 0.135 ± 0.01 | 0.259 ± 0.01 |
| 5 | 0.181 ± 0.03 | 0.160 ± 0.01 | 0.320 ± 0.01 |
| 7 | 0.063 ± 0.02 | 0.168 ± 0.02 | 0.343 ± 0.03 |

Results

As can be seen in Table 3, control cells demonstrated, over time, the expected progressive increase in the average amount of protein per cell. Thus, the protein per cell on day one was approximately 0.1 nanograms per cell and this had almost doubled (0.18 nanograms/cell) by day five. Between day 5 and day 7, the majority of cells in the control sample divided and the average protein per cell had dropped to approximately 0.06 nanograms protein per cell, reflecting the smallest, post-mitotic cell size. This pattern is consistent with the reported doubling time for this cell line.

In contrast to this normal pattern, the 1-fluoro-myo-inositol treated cells showed an arrest in their cell cycle. Cellular size on day one was approximately the same as that of controls (as expected) and the amount of protein per cell steadily increased to a plateau approximately twice that of the protein levels on day one. Thus, cells treated with 1-fluoro-myo-inositol were able to continue to increase in size up to the point at which they should receive a signal to divide. However, this signal was apparently lacking and cells arrested in a pre-mitotic state (termed late G2), as reflected by their size, which was approximately 2-fold greater than controls.

In contrast to both the control and 1-fluoro-myo-inositol treated cells, the 3-fluoro-myo-inositol treated cells demonstrated a most remarkable and unique pattern of cell growth. These cells likewise began with normal levels of cellular protein reflecting a normal size. However, these cells continued to increase steadily in size without undergoing cell division. Thus, by day seven, 3-fluoro-myo-inositol treated cells had increased to a size about 3.5 times as large as control cells. Nevertheless, the rate of cell replication had slowed considerably, as indicated by EXAMPLE XII. Thus, it seems that the 3-fluoro-myo-inositol compound disrupts the ability of the cell to initiate mitosis (i.e., cell division), but that cell size continues to increase. This indicates fundamental desynchronization of the internal signaling systems of the cell with regard to control of cell replication and cell division, which involve the conjoint regulation of cell size and cell replication.

EXAMPLE XV

Effects of 1-deoxy-1-Fluoro and 3-deoxy-3-Fluoro-Myo-inositol Analog on Inositol Transport

Background

To determine if the effect of the fluoro-myo-inositol analogs might be mediated by the blockade of the myo-inositol transporter, which is responsible for uptake and accumulation of myo-inositol into the cell, the ability of these two compounds to block [$^3$H]myo-inositol transport was studied directly.

Method

The uptake of [$^3$H]myo-inositol by the myo-inositol transporter was determined as follows:

PC12 cells were gently detached and maintained in a suspension culture in RPMI medium (both myo-inositol and serum free) at 37° C. [$^3$H]myo-inositol was added to this culture at a concentration of 1μCi/ml. Aliquots of this suspension were removed at the indicated time, diluted in 10 volumes of ice-cold PBS containing 10 mM unlabelled myo-inositol to stop the uptake process, centrifuged at 4° C. for 20 minutes at 50xg. The cell pellet, which contained the transported [$^3$H]myo-inositol, was dissolved in dilute NaOH and the radioactivity quantified by liquid scintillation counting. The results, shown in Table 4, were as follows:

TABLE 4

Effects of 1-deoxy-1-Fluoro and 3-deoxy-3-Fluoro Myo-Inositol Analogs on Inositol Transport

| Compound | Affinity Constant $K(\mu M)$ | Maximal Transport Rate Vmax (nMol/mg/hr) |
|---|---|---|
| Myo-inositol | 45 | 2.27 |
| 1-Fluoro-myo-inositol analog | 1,430 | 2.27 |
| 3-Fluoro-myo-inositol analog | 250 | 2.27 |

The Ka and Vmax of myo-inositol were determined from Lineweaver-Burke plots of the uptake of [$^3$H]myo-inositol (25 nM) in the presence of increasing concentrations of unlabeled myo-inositol in PC12 cells. The Ki of the two fluoro-myo-inositol analogs was determined by conducting the uptake studies in the presence of a fixed concentration (1 mM) of each myo-inositol analog.

These results indicate that the 1-fluoro and 3-fluoro-myo-inositol analogs did block [$^3$H]myo-inositol uptake, but with a reversed potency compared to their effects on cellular replication. Indeed, the 3-fluoro myo-inositol analog was 5.7 times as potent as the 1-fluoro myo-inositol analog in blocking myo-inositol transport. These results demonstrated that the growth inhibitory effects of 1-fluoro and 3-fluoro myo-inositol analogs accrued distal to the transport site for myo-inositol, since there was a reversed selectivity for these two analogs with regard to their growth and transport inhibitory effects.

EXAMPLE XVI

Effects of Fluoroinositol Analogs on Inositol Incorporation into Cell Plasma Membranes

Background

The results described hereinabove demonstrate that 1-deoxy-1-fluoro and 3-deoxy-3-fluoro-myo-inositol analog are capable of inhibiting cellular replication in a dose dependent manner. Furthermore, the mechanism of this inhibition involves the intracellular myo-inositol signalling pathways since the 1-fluoro-myo-inositol analog was 5-fold more potent than the 3-fluoro-myo-inositol analog at inhibiting cell replication, but had an affinity for the myo-inositol transporter that was 5.7-fold lower than the 3-fluoro-myo-inositol analog.

Since myo-inositol must be incorporated into the cellular plasma membranes in order for it to serve its role as a second messenger, we therefore verified the ability of the 1- and 3-fluoro-myo-inositol analogs to perturb the incorporation of myo-inositol into cellular plasma membranes by the enzyme CDP-diacylglycerol-inositol phosphatidyltransferase (phosphatidylinositol synthetase).

We predicted that cells exposed to the 1-fluoro-myo-inositol analog would be unable to incorporate any myo-inositol into their cellular plasma membranes, since the 1 position necessary for the myo-inositol-diacylglycerol linkage was blocked by the fluorine at this position. In contrast, we predicted that the 3-fluoro-myo-inositol compound would be incorporated into the cellular plasma membranes since the 1 position was free.

These tests were conducted by treating cells for either 1, 3, 5, or 7 days with the myo-inositol analogs, followed by a brief exposure to radiolabeled myo-inositol ($[^3H]$myo-inositol). The extent of incorporation of tritiated myo-inositol would, therefore, reflect the extent to which phosphatidylinositol and its phosphorylated analogs are deficient in the cellular plasma membranes.

Methods

Cells were grown as described hereinabove. Twenty-four hours after plating, the medium was changed and cells were exposed to either inositol free medium (Control 2) or medium containing either the 1- or the 3-fluoro-myo-inositol analog. At four different time points—1, 3, 5, and 7 days—cells were tested for their ability to incorporate radio labeled $[^3H]$myo-inositol. This test was conducted by removing the medium and replacing it with RPMI medium (both myo-inositol and serum free) containing only $[^3H]$myo-inositol The cells were exposed to this medium for a period of one hour, following which they were washed three times with phosphate-buffered saline containing excess unlabeled myo-inositol (10 mM). Cells were lysed by treatment with trichloroacetic acid (TCA) and sonicated to insure complete disruption. The cellular homogenate was then collected and spun in a microfuge tube at 12,000 r.p.m. for 15 min. Samples from both the pellet and supernatant were then obtained and the levels of radioactivity in each were determined. Radioactivity in the supernatant corresponded to the amount of free $[^3H]$myo-inositol in the cytoplasm of the cell, whereas the radioactivity present in the TCA-precipated pellet represented $[^3H]$myo-inositol incorporated into the cellular plasma membranes.

Results

The results, shown in Table 5, were as follows:

TABLE 5

| | Uptake and Incorporation of $[^3H]$myo-inositol into PC12 Cells Following Treatment with Inositol Analogs | | | | | |
|---|---|---|---|---|---|---|
| | Control | | 1-deoxy-1-Fluoro-Ins | | 3-deoxy-3-Fluoro-Ins | |
| Day | Free | Bound | Free | Bound | Free | Bound |
| 1 | 8840 ± 146 | 367 ± 15 | 8365 ± 787 | 392 ± 16 | 3326 ± 253 | 354 ± 10 |
| 3 | 3749 ± 776 | 794 ± 128 | 4751 ± 291 | 4614 ± 141 | 2929 ± 189 | 761 ± 42 |
| 5 | 3967 ± 449 | 759 ± 119 | 4295 ± 627 | 2143 ± 314 | 2900 ± 383 | 414 ± 52 |
| 7 | 1942 ± 484 | 397 ± 100 | 7569 ± 757 | 3726 ± 588 | 4095 ± 161 | 676 ± 113 |

Cells were treated for the indicated time periods with the inositol analogs, and then exposed for one hour to $[^3H]$myo-inositol. Numbers represent DPM/$10^6$ cells.

As can be seen, this procedure allowed for the uptake of a significant amount of radiolabeled myo-inositol. Control cells demonstrated a robust uptake of radiolabeled myo-inositol into the cytoplasm on all days examined, but only a relatively small fraction of the total radioactive myo-inositol (ranging from 4% on day one to 17% on day seven) was actually incorporated into the cellular plasma membranes after being transported into the cell. This is consistent with our understanding that myo-inositol is of vital importance for the maintenance of cell cycle control and that the majority of sites available for linkage to myo-inositol in the cellular plasma membranes are occupied by myo-inositol at all times.

In contrast, cells treated with the 1-fluoro-myo-inositol analog demonstrated a very different pattern of incorporation. On day one, these cells were not remarkably different from control cells in either the amount of free or incorporated $[^3H]$myo-inositol. However, these cells rapidly became myo-inositol deficient as evidenced by their marked incorporation of radiolabeled myo-inositol into the cellular plasma membranes on days 3, 5, and 7. Thus, after only several days of exposure to the 1-fluoro-myo-inositol analog, there was a 10-fold increase in the number of unoccupied sites for myo-inositol in the cellular plasma membranes. This is consistent with the ability of 1-fluoro-myo-inositol analog to compete for myo-inositol uptake, but once inside the cell, to be an inactive substrate for the key enzyme phosphatidylinositol synthetase (CDP-diacylglycerol-inositol phosphatidyltransferase; E.C.2.7. 8.11), which catalyses the linkage of myo-inositol to phosphatidic acid, which is present in the cellular plasma membranes.

The effects of the 3-fluoro-myo-inositol analog were also consistent with our predictions. Although the cells continued to be able to accumulate myo-inositol without difficulty, the level of radioactively-labeled myo-inositol that was incorporated into the cellular plasma membranes was quite low. This indicates that the 3-fluoro-myo-inositol analog did serve as a substrate for inositol synthetase and that the membrane sites for myo-inositol were indeed occupied by the 3-fluoro-myo-inositol analog.

Accordingly, the 1- and the 3-fluoro-myo-inositol analogs would be expected to disrupt the phosphatidylinositol cycle at different points. Furthermore, 1-fluoro-myo-inositol should disrupt myo-inositol signaling completely, whereas the 3-fluoro-myo-inositol analog compound should disrupt signaling mediated by myo-inositol compounds phosphorylated at the 3 position.

These results further provide conclusive evidence that both the 1-fluoro and 3-fluoro myo-inositol analogs serve as inhibitors of cell growth based upon their ability to interfere with phosphatidylinositol cycle. Accordingly, these fluoro-myo-inositol analogs should have utility in a variety of settings in which the transmission of signals via the phosphatidylinositol pathway is of importance. For example, these compounds should be useful in the study of cell growth, both in vivo and in vitro, as well as in the treatment of disorders in which cellular proliferation is disturbed. However, the phosphatidylinositol cycle is of fundamental importance for a number of physiological processes unrelated to cell replication, so that these compounds should find utility in other areas as well. By way of example, the activation of many neurotransmitter receptors is known to result in the stimulation of the PI cycle. Accordingly, the study of neural function as it relates to the PI cycle should be facilitated by the use of these compounds. Furthermore, these compounds should find utility in the treatment of disorders in which excessive neurotransmitter activity has been implicated. For example, lithium salts have been used for many years in the treatment of bipolar mood disorder, and it is now known that lithium blocks the PI cycle, as do the inositol analogs described hereinabove. Accordingly, these compounds should find utility in the treatment of bipolar disorder. Inositol signaling pathways are also known to be important in the proper functioning of important blood elements (e.g., lymphocytes, leukocytes, platelets) and the analogs described hereinabove should be useful in the study of these systems as well as the treatment of certain disorders of these systems. The examples given above are incorporated solely for the purpose of illustrating the known importance of the PI cycle, and the utility to be derived from compounds capable of inhibiting the PI cycle. Therefore, the utility of these compounds should not be construed as being limited to the few examples described hereinabove.

What is claimed is:

1. A compound represented by the general formula II:

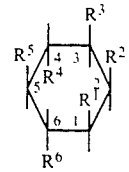

wherein:

$R^1$, $R^2$, $R^3$, $R^4$, $R^5$ and $R^6$ is each independently selected from the group consisting of OH, F, $N_3$, $NH_2$, SH, SeH, Cl Br, I and CN; with the proviso:

(i) four or five of said $R^1$, $R^2$, $R^3$, $R^4$, $R^5$ and $R^6$ are OH;

(ii) if one of said $R^1$, $R^2$, $R^3$, $R^4$, $R^5$ and $R^6$ is $N_3$, then one of said $R^1$, $R^2$, $R^3$, $R^4$, $R^5$ and $R^6$ is selected from the group consisting of F, $NH_2$, SH, SeH, Cl, Br, I and CN;

(iii) if one of said $R^1$, $R^{12}$, $R^3$, $R^4$, $R^5$ and $R^6$ is $NH_2$, then one of said $R^1$, $R^2$, $R^3$, $R^4$, $R^5$ and $R^6$ is selected from the group consisting of F, $N_3$, SH, SeH, Cl, Br, I and CN; and (iv) if said $R^4$, $R^5$ or $R^6$ is F, Cl, Br or I then four of said $R^1$, $R^2$, $R^3$, $R^4$, $R^5$ and $R^6$ are OH.

2. A compound according to claim 1 wherein five of said $R^1$, $R^2$, $R^3$, $R^4$, $R^5$ and $R^6$ are OH.

3. The compound of claim 1 wherein one of said $R^1$, $R^2$, $R^3$, $R^4$, $R^5$ and $R^6$ is F or SH.

4. The compound method of claim 3 wherein one of said $R^1$, $R^2$, $R^3$, $R^4$, $R^5$ and $R^6$ is F.

5. The compound of claim 1 wherein $R^1$ is selected from the group consisting of F, SH, SeH, Cl, Br, I and CN.

6. The compound of claim 5 wherein $R^1$ is F or SH.

7. The compound of claim 6 wherein $R^1$ is F.

8. The compound of claim 1 wherein $R^3$ is selected from the group consisting of F, SH, SeH, Cl, Br, I and CN.

9. The compound of claim 8 wherein $R^3$ is F or SH.

10. The compound of claim 9 wherein $R^3$ is F.

11. The compound of claim 1 wherein four of said $R^1$, $R^2$, $R^3$, $R^4$, $R^5$ and $R^6$ are OH.

12. The compound of claim 11 wherein two of said $R^1$, $R^4$ and $R^5$ are independently selected from the group consisting of F, $N_3$, $NH_2$, SH, SeH, Cl, Br, I and CN.

13. The compound of claim 12 wherein said $R^4$ and $R^5$ are independently selected from the group consisting of F, $N_3$, $NH_2$, SH, SeH, Cl, Br I and CN.

14. The compound of claim 11 wherein two of said $R^1$, $R^2$, $R^3$, $R^4$, $R^5$ and $R^6$ are selected from the group consisting of F and SH; F and $NH_2$; $NH_2$ and SH; SH and SH; and F and F.

15. The compound of claim 14 wherein two of said $R^1$, $R^2$, $R^3$, $R^4$, $R^5$ and $R^6$ are F and F.

16. A pharmaceutical composition comprising a therapeutically effective amount for inhibiting the phosphatidylinositol cycle in a manual of a compound represented by the general formula III:

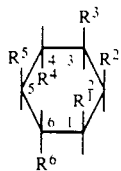

III wherein:
$R^1$, $R^2$, $R^3$, $R^4$, $R^5$, and $R^6$ is each independently selected from the group consisting of OH, F, $N_3$, $NH_2$, SH, SeH, Cl, Br, I and CN; with the proviso:

(i) four or five of said $R^1$, $R^2$, $R^3$, $R^4$, $R^5$, and $R^6$ are OH;
(ii) if one of said $R^1$, $R^2$, $R^3$, $R^4$, $R^5$ and $R^6$ is $N_3$, then one of said $R^1$, $R^2$, $R^3$, $R^4$, $R^5$, and $R^6$ is selected from the group consisting of F, $NH_2$, SH, SeH, Cl, Br, I and CN;
(iii) if one of said $R^1$, $R^2$, $R^3$, $R^4$, $R^5$, and $R^6$ is $NH_2$, then one of said $R^1$, $R^2$, $R^3$, $R^4$, $R^5$, and $R^6$ is selected from the group consisting of F, $N_3$, SH, SeH, Cl, Br, I and CN; and
(iv) if said $R^4$, $R^5$, and $R^6$ is F, Cl, Br, or I then four of said $R^1$, $R^2$, $R^3$, $R^4$, $R^5$, and $R^6$ are OH, and a pharmaceutically acceptable carrier.

* * * * *

UNITED STATES PATENT AND TRADEMARK OFFICE
CERTIFICATE OF CORRECTION

PATENT NO. : 4,988,682

DATED : January 29, 1991

INVENTOR(S) : Alan P. Kozikowski

Page 1 of 6

It is certified that error appears in the above-identified patent and that said Letters Patent is hereby corrected as shown below:

Column 8, line 52 after "zene" and before "The" insert -- . --.

Columns 11-12, lines 23-32, delete:

" 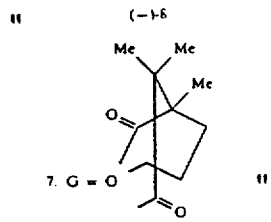 and insert in place therefore: -- 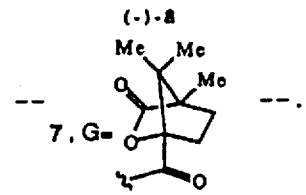 --.

Column 16, lines 27-33, delete:

" 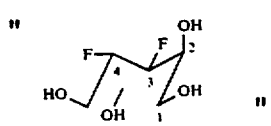 and insert in place therfore: -- 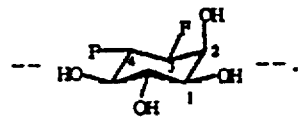 --.

Column 17, lines 2-7, delete:

" 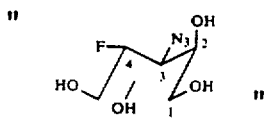 and insert in place therefore: -- 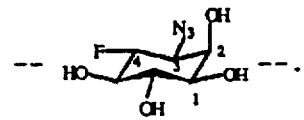 --.

Column 17, line 17, delete "EXAMPLE IV" and insert in place therefore: -- EXAMPLE VI --.

Column 17, lines 44-49, delete:

" 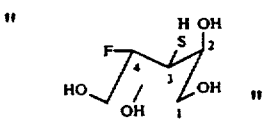 and insert in place therefore: -- 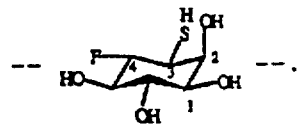 --.

UNITED STATES PATENT AND TRADEMARK OFFICE
CERTIFICATE OF CORRECTION

PATENT NO. : 4,988,682

DATED : January 29, 1991

INVENTOR(S) : Alan P. Kozikowski

It is certified that error appears in the above-identified patent and that said Letters Patent is hereby corrected as shown below:

Column 19, lines 30-59, delete:

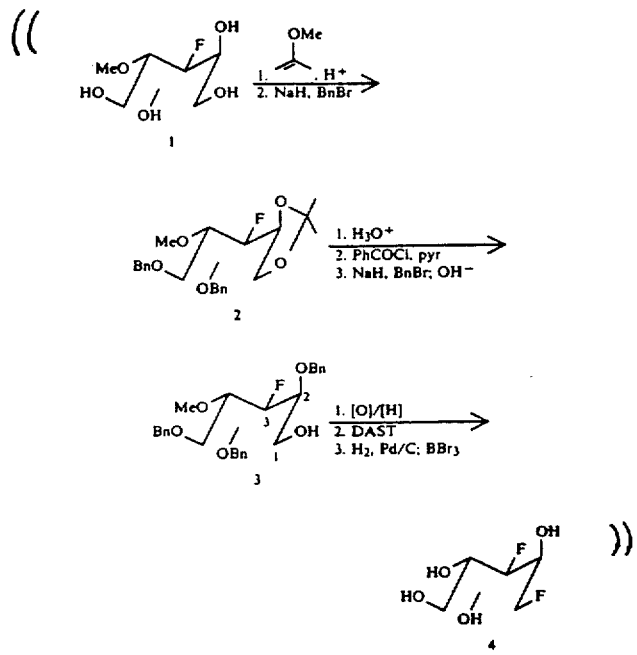

UNITED STATES PATENT AND TRADEMARK OFFICE
CERTIFICATE OF CORRECTION

PATENT NO. : 4,988,682

DATED : January 15, 1991

INVENTOR(S) : Alan P. Kozikowski

It is certified that error appears in the above-identified patent and that said Letters Patent is hereby corrected as shown below:

and insert in place therefore:

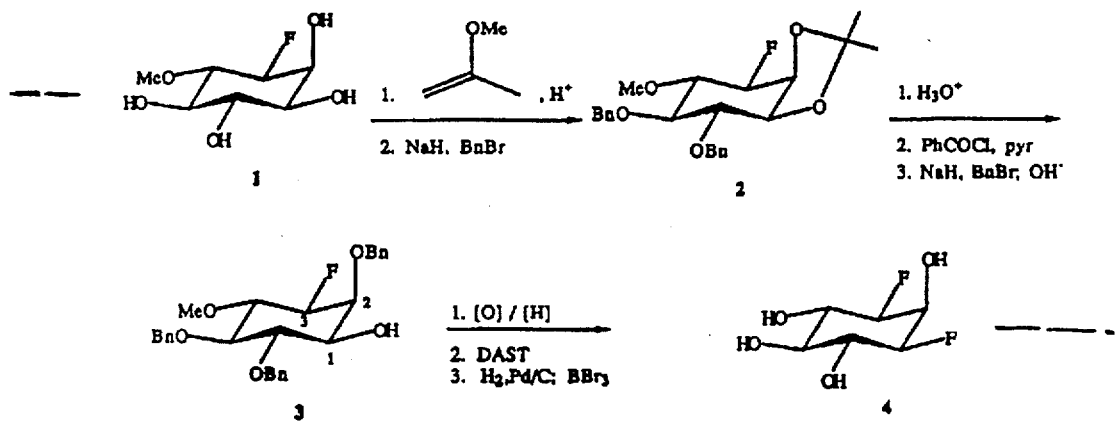

UNITED STATES PATENT AND TRADEMARK OFFICE
CERTIFICATE OF CORRECTION

PATENT NO. : 4,988,682

DATED : January 29, 1991

INVENTOR(S) : Alan P. Kozikowski

It is certified that error appears in the above-identified patent and that said Letters Patent is hereby corrected as shown below:

Column 20, lines 5-23, delete:

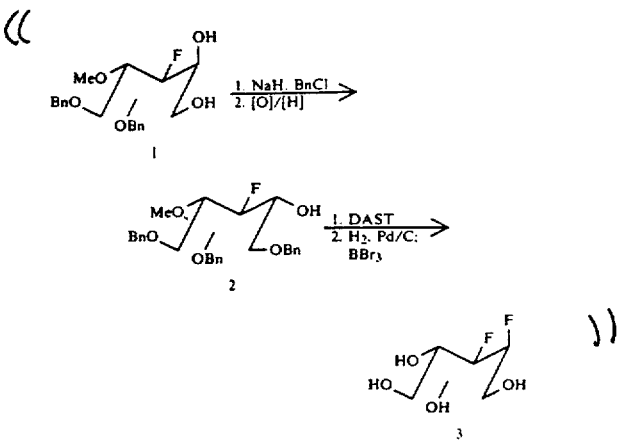

and insert in place therefore:

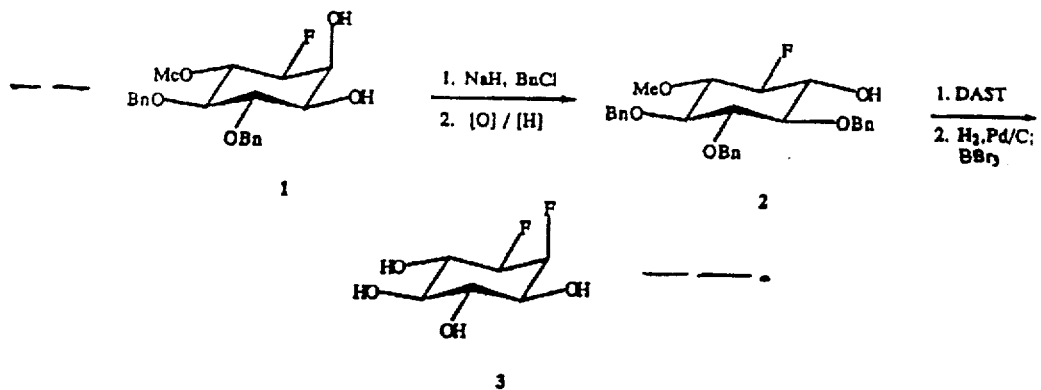

UNITED STATES PATENT AND TRADEMARK OFFICE
CERTIFICATE OF CORRECTION

PATENT NO. : 4,988,682

DATED : January 29, 1991

INVENTOR(S) : Alan P. Kozikowski

It is certified that error appears in the above-identified patent and that said Letters Patent is hereby corrected as shown below:

Column 20, lines 36-56, delete:

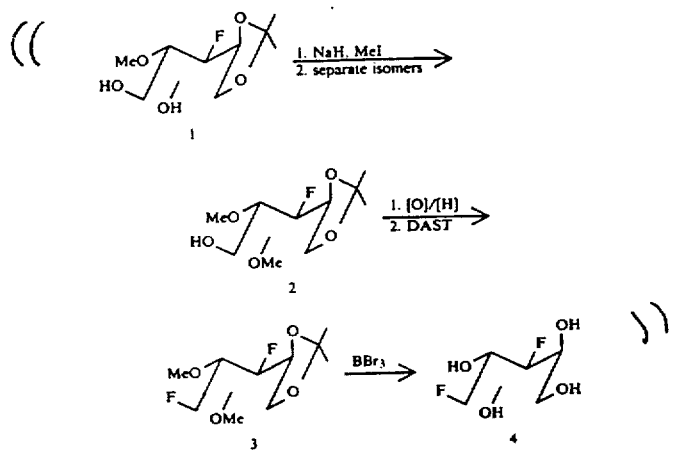

UNITED STATES PATENT AND TRADEMARK OFFICE
CERTIFICATE OF CORRECTION

PATENT NO.  : 4,968,682

Page 6 of 6

DATED       : January 29, 1991

INVENTOR(S) : Alan P. Kozikowski

It is certified that error appears in the above-identified patent and that said Letters Patent is hereby corrected as shown below:

and insert in place therefore:

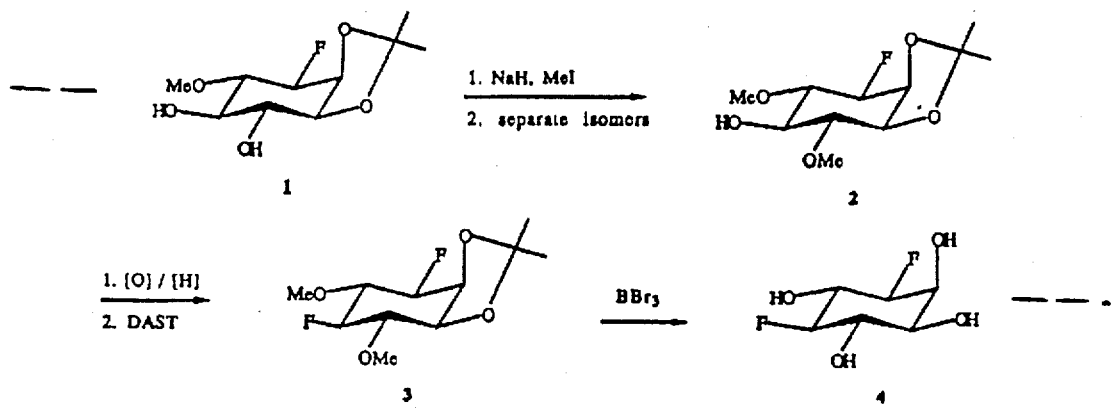

Column 28, line 67, delete "manual" and insert in place therefore: -- mammal --.

Signed and Sealed this

Twenty-second Day of December, 1992

*Attest:*

DOUGLAS B. COMER

*Attesting Officer*   *Acting Commissioner of Patents and Trademarks*